(12) United States Patent
Kavallar et al.

(10) Patent No.: US 10,279,102 B2
(45) Date of Patent: May 7, 2019

(54) DEVICE AND METHOD FOR MOUNTING A PHARMACEUTICAL APPLICATION AID

(71) Applicant: ARZNEIMITTEL GmbH APOTHEKER VETTER & CO. RAVENSBURG, Ravensburg (DE)

(72) Inventors: Guenter Kavallar, Aulendorf (DE); Hubert Goederle, Paffenhofen a.d. Roth (DE); Janosch Steib, Ummedorf (DE)

(73) Assignee: ARZNEIMITTAL GMBH APOTHEKER VETTER & CO. RAVENSBURG, Ravensburg (DE)

( * ) Notice: Subject to any disclaimer, the term of this patent is extended or adjusted under 35 U.S.C. 154(b) by 579 days.

(21) Appl. No.: 14/814,565

(22) Filed: Jul. 31, 2015

(65) Prior Publication Data
US 2015/0335814 A1 Nov. 26, 2015

Related U.S. Application Data

(63) Continuation of application No. 12/741,070, filed as application No. PCT/EP2008/009268 on Nov. 4, 2008, now Pat. No. 9,107,984.

(30) Foreign Application Priority Data

Nov. 7, 2007 (DE) .................. 10 2007 054 868

(51) Int. Cl.
*A61M 5/24* (2006.01)
*A61M 5/00* (2006.01)
*A61M 5/178* (2006.01)

(52) U.S. Cl.
CPC .............. *A61M 5/00* (2013.01); *A61M 5/002* (2013.01); *A61M 5/1782* (2013.01); *A61M 5/2448* (2013.01); *A61M 2205/14* (2013.01); *A61M 2207/00* (2013.01); *A61M 2207/10* (2013.01); *A61M 2209/08* (2013.01); *A61M 2209/082* (2013.01); *Y10T 29/49766* (2015.01); *Y10T 29/49771* (2015.01); *Y10T 29/49826* (2015.01); *Y10T 29/49828* (2015.01);
(Continued)

(58) Field of Classification Search
CPC ...... A61M 5/00; A61M 5/002; A61M 5/1782; A61M 5/2448; A61M 5/24; A61M 5/3287; Y10T 29/49826; Y10T 29/49904; Y10T 29/53539
See application file for complete search history.

(56) References Cited

U.S. PATENT DOCUMENTS 4,833,384 A * 5/1989 Munro ................ A61M 5/1452
128/DIG. 1
4,950,246 A * 8/1990 Muller ................ A61M 5/1452
128/DIG. 1
(Continued)

*Primary Examiner* — A. Dexter Tugbang
*Assistant Examiner* — Kaying Kue
(74) *Attorney, Agent, or Firm* — Stephen T. Olson; Harness, Dickey & Pierce, P.L.C.

(57) ABSTRACT

A device (1) for assembly of a pharmaceutical application aid (51), particularly a pen, is proposed. The device (1) is characterized by a holding device (3) for fixation of a first housing sleeve (5) that accommodates a pharmaceutical container, particularly a carpule (23), and by a stop (43) for limiting a displacement of a second housing sleeve (35) relative to the first housing sleeve (5).

21 Claims, 5 Drawing Sheets

Figure 1:
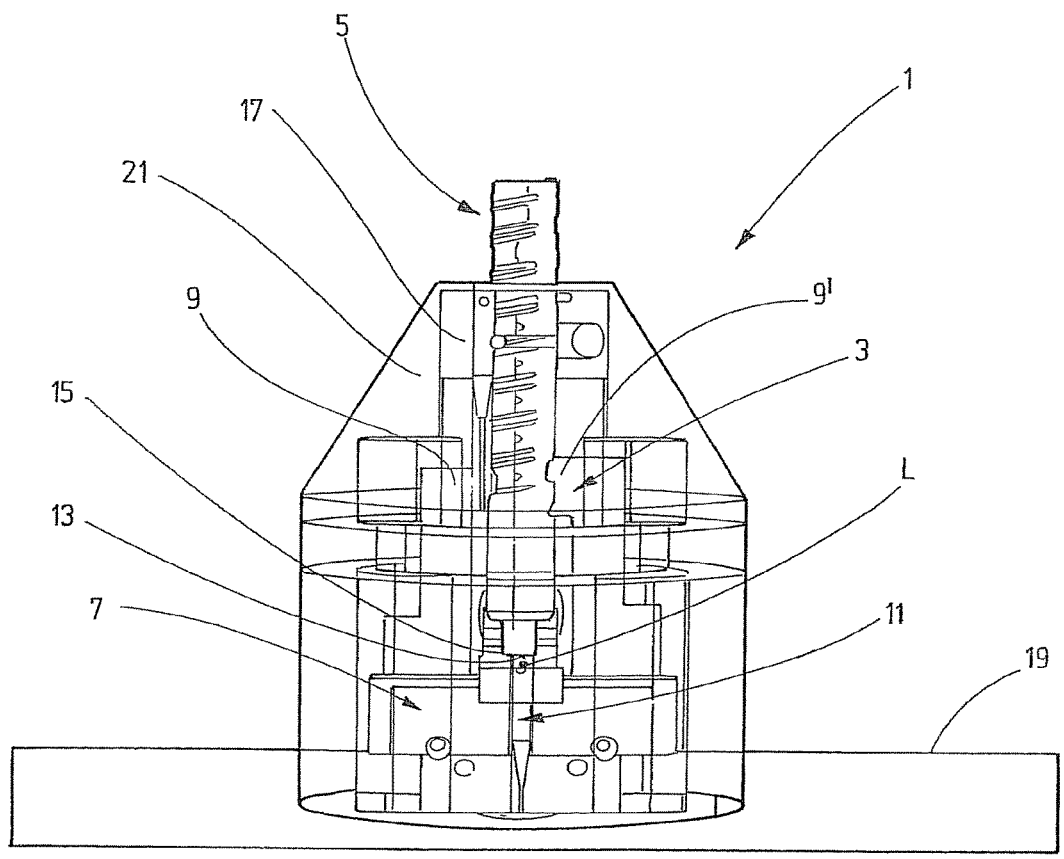

(52) U.S. Cl.
CPC .... *Y10T 29/53061* (2015.01); *Y10T 29/53539* (2015.01); *Y10T 29/53961* (2015.01)

(56) References Cited

U.S. PATENT DOCUMENTS

| | | | | |
|---|---|---|---|---|
| 5,137,516 | A * | 8/1992 | Rand | A61J 1/00 604/136 |
| 5,139,484 | A * | 8/1992 | Hazon | A61M 5/1456 128/DIG. 1 |
| 5,593,390 | A * | 1/1997 | Castellano | A61M 5/31553 604/187 |
| 5,728,074 | A * | 3/1998 | Castellano | A61M 5/31553 604/207 |
| 5,925,021 | A * | 7/1999 | Castellano | A61M 5/31553 604/207 |
| 6,042,571 | A * | 3/2000 | Hjertman | A61M 5/14566 604/208 |
| 6,585,698 | B1 * | 7/2003 | Packman | A61M 5/24 604/207 |
| 6,689,118 | B2 * | 2/2004 | Alchas | A61M 5/158 604/117 |
| 6,692,469 | B1 * | 2/2004 | Weekes | A61M 5/002 604/137 |
| 6,776,776 | B2 * | 8/2004 | Alchas | A61M 5/3129 604/117 |
| 7,214,209 | B2 * | 5/2007 | Mazzoni | A61M 15/0028 604/131 |
| 7,252,651 | B2 * | 8/2007 | Haider | A61M 5/2033 604/137 |
| 7,258,119 | B2 * | 8/2007 | Mazzoni | A61M 15/0028 128/200.14 |
| 7,628,773 | B2 * | 12/2009 | Graf | A61M 5/31553 604/207 |
| 7,704,231 | B2 * | 4/2010 | Pongpairochana | A61M 5/20 604/134 |
| 8,052,655 | B2 * | 11/2011 | Moller | A61M 5/31553 604/246 |
| 8,221,359 | B2 * | 7/2012 | Kristensen | A61M 5/3202 604/110 |
| 8,439,838 | B2 * | 5/2013 | Mogensen | A61B 5/14532 600/365 |
| 8,556,867 | B2 * | 10/2013 | Krulevitch | A61M 5/24 604/223 |
| 8,708,957 | B2 * | 4/2014 | Jespersen | A61M 5/1452 604/135 |
| 8,734,402 | B2 * | 5/2014 | Sharp | A61M 5/002 604/198 |
| 8,771,233 | B2 * | 7/2014 | Watanabe | A61M 5/14546 604/189 |
| 8,801,679 | B2 * | 8/2014 | Iio | A61M 5/20 604/263 |
| 8,808,228 | B2 * | 8/2014 | Brister | A61B 5/0002 604/66 |
| 8,932,252 | B2 * | 1/2015 | Edwards | G06Q 10/00 604/131 |
| 2005/0090781 | A1 * | 4/2005 | Baba | G06F 19/00 604/209 |

* cited by examiner

DEVICE AND METHOD FOR MOUNTING A PHARMACEUTICAL APPLICATION AID

CROSS-REFERENCE TO RELATED APPLICATIONS

This application is a continuation of U.S. application Ser. No. 12/741,070 filed 3 May 2010, which is a 371 U.S. National Stage of International Application No. PCT/EP2008/009268 filed 4 Nov. 2008, which claims the benefit of German Patent Application No. DE 10 2007 054 868.2 filed Nov. 7, 2007, the disclosures of the which applications are incorporated herein by reference.

The invention relates to a device for assembly of a pharmaceutical application aid, as well as to a method for assembly of a pharmaceutical application aid. The invention also relates to the use of a device for assembly of a pharmaceutical application aid.

Application aids of the type being discussed here are known. These are, in particular, so-called pens or auto-injectors, which typically are used in insulin therapy, in cases of diabetes mellitus. Application aids such as pens allow easier transport, uncomplicated handling by the user, and precise metering. A further advantage of pens is their inconspicuous use. Single-use pens that are filled and ready for use, and contain an ampule configured as a non-replaceable carpule are available. Also, pens are available whose ampule is replaceable and can issue multiple doses of a specific medication. The carpules used can be carpules for normal syringe uses, but also special dual-chamber carpules for accommodating a lyophilisate. Application aids of the type being discussed here typically comprise a first housing sleeve into which the carpule is introduced, and a second housing sleeve that is joined together with the first housing sleeve by way of a screw connection or a plug-in connection, for example. A piston rod is disposed in the second housing sleeve, which rod serves to displace the stopper of the carpule and thus serves for injection. In fully automatic assembly of such application aids, devices for joining the two housing sleeves together by machine are provided, which allow precise positioning of the two housing sleeves relative to one another. In semi-automatic assembly of such application aids, in contrast, the second housing sleeve is screwed onto or set onto the first housing sleeve by hand. Semi-automatic assembly of application aids is particularly used if only small numbers of units are supposed to be produced, for which the use of a fully automatic assembly unit is not worthwhile, because of the significant costs.

It has been shown, in the semi-automatic assembly of application aids, that the second housing sleeve is often screwed or set too far onto the first housing sleeve, so that the piston rod disposed in the second housing sleeve displaces the stopper of the carpule disposed in the first housing sleeve. As a result of the displacement of the stopper, activation of a lyophilisate in a dual-chamber carpule or exit of an injection preparation from a conventional carpule can occur. Such activation of the injection preparation before actual use by the patient is undesirable and leads to the result that the application aid becomes unusable. In particular, there is the risk that activation of the carpule contents is not noticed, particularly in the case of dual-chamber carpules.

It is therefore the task of the present invention to create a device for assembly of a pharmaceutical application aid, particularly of a pen, which avoids the disadvantage indicated above, in other words prevents two housing sleeves from being screwed too far into one another during the assembly of an application aid.

To accomplish this task, a device for assembly of a pharmaceutical application aid, particularly a pen is characterized by a holding device for fixation of a first housing sleeve and by a stop for limiting a displacement of a second housing sleeve relative to the first housing sleeve. By means of the advantageous combination of a holding device for axial and radial fixation of the first housing sleeve with a stop for limiting the displacement path of the second housing sleeve, overly great displacement of the second housing sleeve relative to the first housing sleeve when joining the two sleeves together is prevented. In this connection, the holding device fixes the first housing sleeve in place in an axial position. In the case of a screw connection between the two housing sleeves, radial fixation by means of the holding device preferably takes place in addition. If the second housing sleeve is now joined together with the first housing sleeve, for example by means of a screw connection or plug-in connection, displacement of the second housing sleeve can only take place up to the stop. Overly great displacement, for example by one rotation too many, or by setting the second housing sleeve on too far, is thus effectively prevented by the stop. Because the first housing sleeve is fixed in place in the holding device, it also cannot be displaced upward into the first housing sleeve, particularly not if a screw connection is provided. By means of the holding device for the first housing sleeve in connection with the stop for the second housing sleeve, an advantageous securing mechanism to prevent activation of the carpule contents is thus created. In total, use of a device for assembly of a pharmaceutical application aid, where the device has the characteristics indicated above, is particularly advantageous.

A particularly preferred device is characterized in that the holding device is operated pneumatically, hydraulically, or magnetically. However, manual activation is also possible. The configuration of the holding device is fundamentally any one that is desired. The deciding factor is that it fixes the first housing sleeve securely in place in a specific position, axially and radially.

Another preferred device is characterized in that at least one first sensor is provided, which detects a specific position of the first housing sleeve in the region of the holding device. In particular, it is provided that the first sensor interacts with the holding device and activates it when the first housing sleeve has reached the specific position. For the first housing sleeve, a stop element can be provided, additionally or also alternatively, which element is situated in the region of the first sensor. It is therefore very well possible to hold the first housing sleeve in a specific position exclusively by activating the holding device by means of the sensor. In order to achieve precise positioning of the first housing sleeve, however, a stop element is advantageous.

In another preferred device, it is provided that an accommodation unit is provided to accommodate the first housing sleeve. Preferably, the accommodation unit encloses the first housing sleeve at least in certain regions. The accommodation unit particularly serves to guide the first housing sleeve until it is detected by the first sensor and/or comes up against the stop element. Furthermore, precise alignment of the first housing sleeve with regard to the holding device is possible by means of the accommodation unit.

Another preferred device is characterized in that the holding device engages into the accommodation unit, at least in certain regions. In this connection, openings can be provided in the accommodation unit, for example, through which gripping elements of the holding device engage in order to fix the first housing sleeve in place. Furthermore, numerous other embodiments of the holding device and of the accommodation unit are also possible; for example, a one-piece configuration of the holding device with the accommodation unit is also possible.

Also, a device is preferred that is characterized in that the stop for the second housing sleeve is configured in one piece with the accommodation unit. In particular, it can be provided that a shoulder is configured on the accommodation unit, which shoulder acts as a stop. However, the stop can also be disposed separate from the accommodation unit, and furthermore, a one-piece configuration of the stop with the holding device is also possible.

Another preferred device is characterized in that at least one second sensor is provided, which detects the contact of the second housing sleeve on the stop. In other words, when the second housing sleeve is joined together with the first housing sleeve, for example screwed onto it, then it can be provided that after one revolution of the second housing sleeve, the latter rests against the stop. The second sensor, which is preferably situated in the region of the stop, then detects the position of the second housing sleeve on the stop. In particular, it can be provided that the second sensor interacts with the holding device and deactivates the holding device after detection of the second housing sleeve in the region of the stop.

Also, a device in which the stop for the second housing sleeve and the stop element for the first housing sleeve are disposed at a defined distance from one another is particularly preferred. The distance between the stop element and the stop is decisive for the fact that no displacement of the stopper in the carpule takes place by means of the piston rod disposed in the second housing sleeve, when the second housing sleeve is joined together with the first housing sleeve. Depending on the length of the housing sleeves and the dimensions of the carpule, this distance can vary.

Finally, a device in which at least one third sensor is provided, which detects the position of the carpule in the first housing sleeve, is also preferred. The third sensor is preferably configured as a laser sensor and generates a corresponding signal if the carpule was correctly disposed in the housing sleeve.

Other characteristics of the device are evident from the dependent claims.

It is furthermore the task of the invention to create a method for assembly of a pharmaceutical application aid, particularly a pen, which avoids the disadvantage mentioned above, in other words prevents two housing sleeves from being screwed into one another too far during assembly of an application aid.

To accomplish this task, a method for assembly of a pharmaceutical application aid, preferably a pen, is proposed. In a first step, the method includes making available a first housing sleeve, furthermore by activating a holding device for fixation of the first housing sleeve in a specific position. Subsequently, introduction of a pharmaceutical container, preferably a carpule, into the first housing sleeve takes place, as does joining together of a second housing sleeve with the first housing sleeve. In a last step, displacement of the second housing sleeve relative to the first housing sleeve takes place, up to a stop that interacts with the second housing sleeve. By means of the method proposed here, for assembly of an application aid, it is prevented, in advantageous manner, that when the second housing sleeve is joined together with the first housing sleeve, excessive tightening takes place, so that the content of a dual-chamber syringe is activated, for example, or an injection preparation exits from a conventional carpule. Because of the fact that the second housing sleeve cannot be displaced further than up to the stop, relative to the first housing sleeve, and that the first housing sleeve, on the other hand, is fixed in place in a specific position by means of the holding device, both radially and axially, it is ensured that activation of the carpule contents, for example by means of accidental over-tightening of the second housing sleeve on the first housing sleeve, resulting in displacement of the carpule stopper, is avoided.

Particularly preferred is a method that is characterized in that in order to achieve the specific position, the first housing sleeve is displaced up to a stop element. By means of the stop element, defined positioning of the first housing sleeve can take place both with regard to the stop and with regard to the holding device. Furthermore, it can be provided that a first sensor detects that the specific position has been reached. This sensor can be provided alternatively or in addition to the stop element. It is also possible to undertake the positioning of the first housing sleeve without a stop element. As soon as the first housing sleeve enters into the region of action of the sensor, the latter must activate the holding device, so that further displacement of the second housing sleeve is not possible.

In another preferred method, it is provided that at least one second sensor detects when the stop is reached. In other words, when the second housing sleeve reaches the stop, this is detected by the second sensor, which furthermore can interact with the holding device. The latter can be deactivated by a corresponding signal of the sensor, so that the completely assembled application aid can be removed from the device.

Another preferred method is characterized in that the first and/or the second sensor interact(s) with at least one display element. It is possible, for example, to use a monitoring light that indicates to the operating personnel that the first sensor has detected the first housing sleeve and/or that the second sensor has detected the second housing sleeve.

Other characteristics of the method are evident from the dependent claims.

To accomplish the task stated above, the device according to the invention can also be used to assemble a pharmaceutical application aid, whereby the advantages described above easily come about.

To accomplish the stated tasks, a device of the type indicated above can also be used to carry out the described method for assembly of an application aid.

Figure 2:
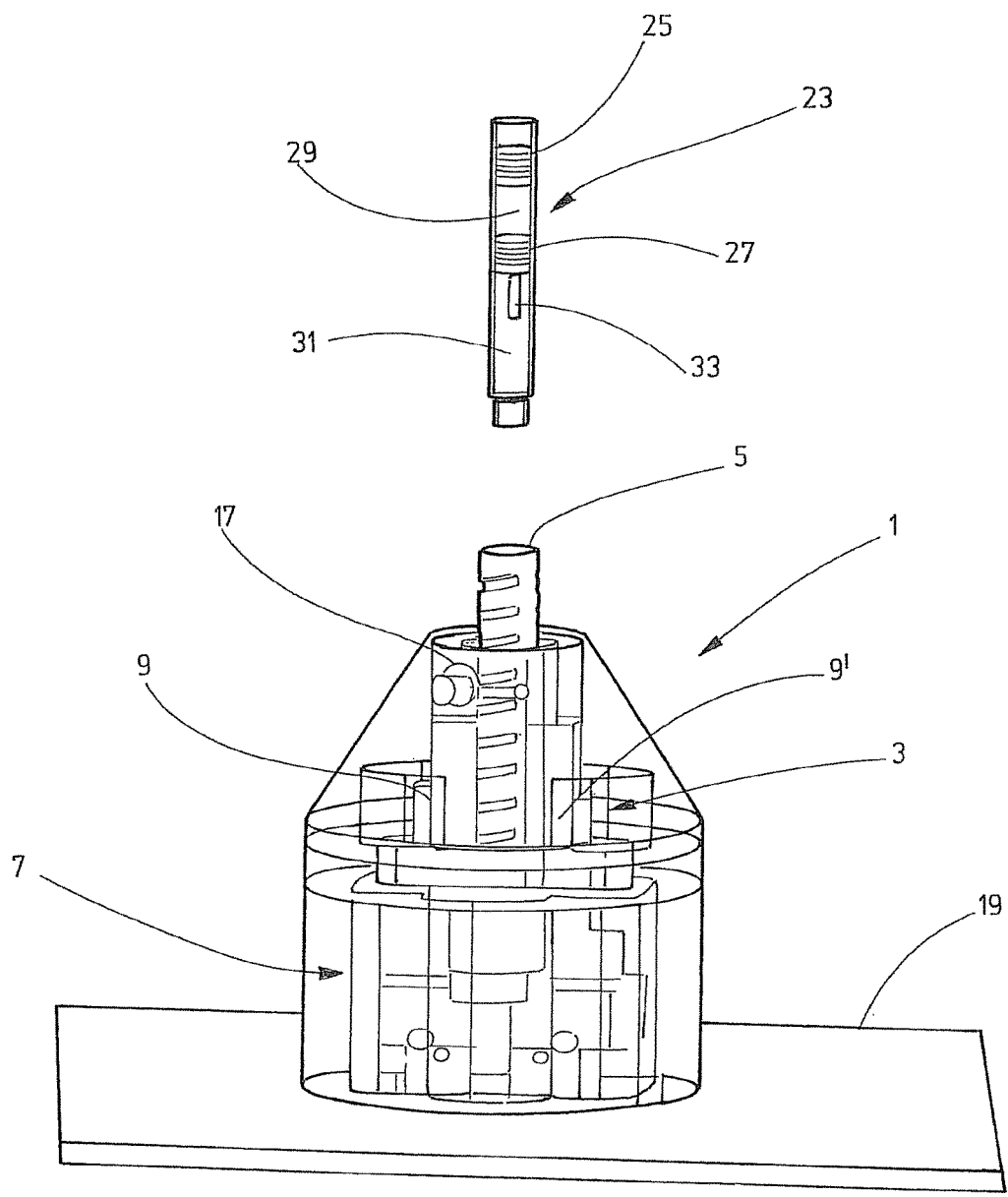
Figure 3:
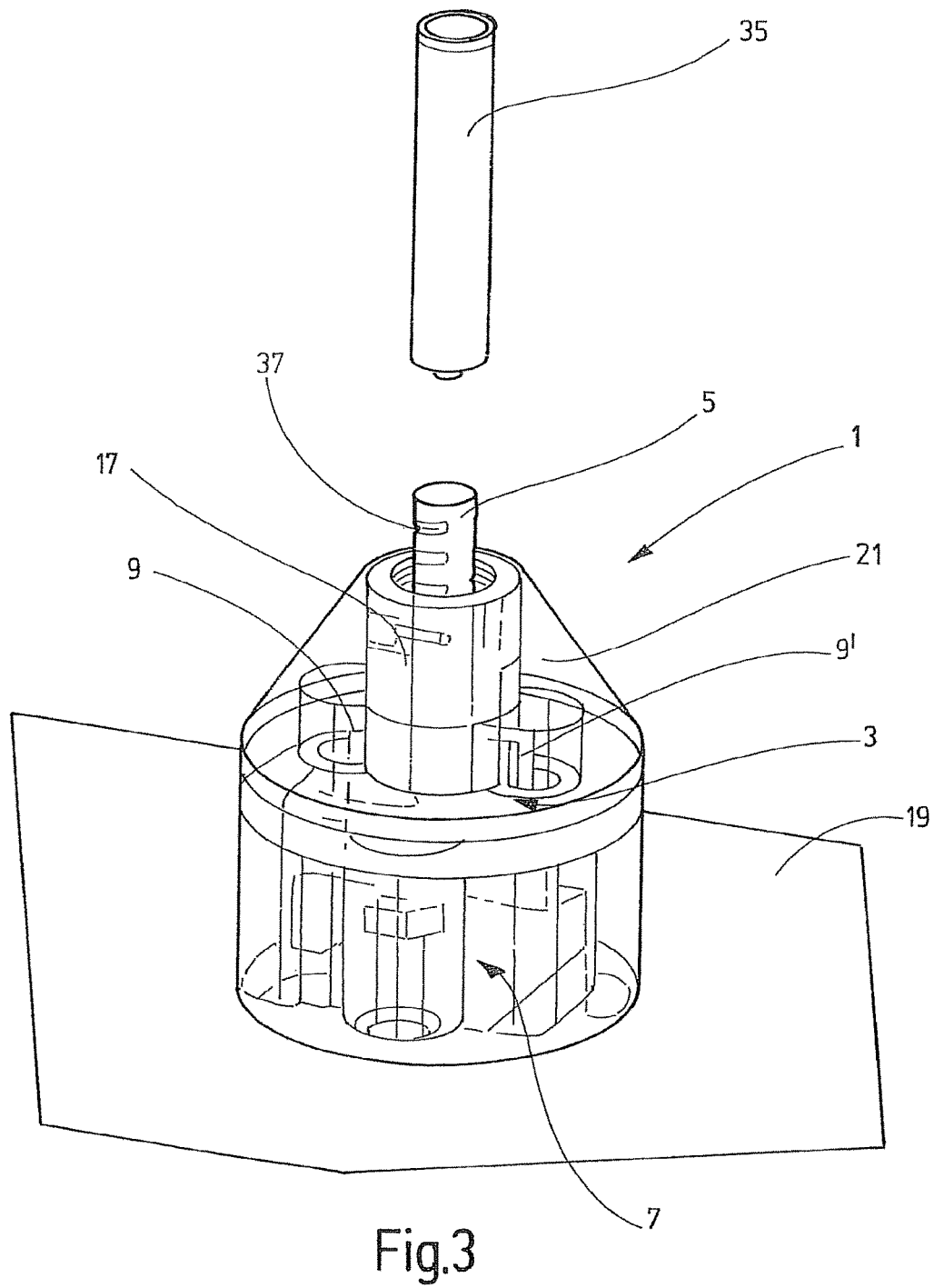
Figure 4:
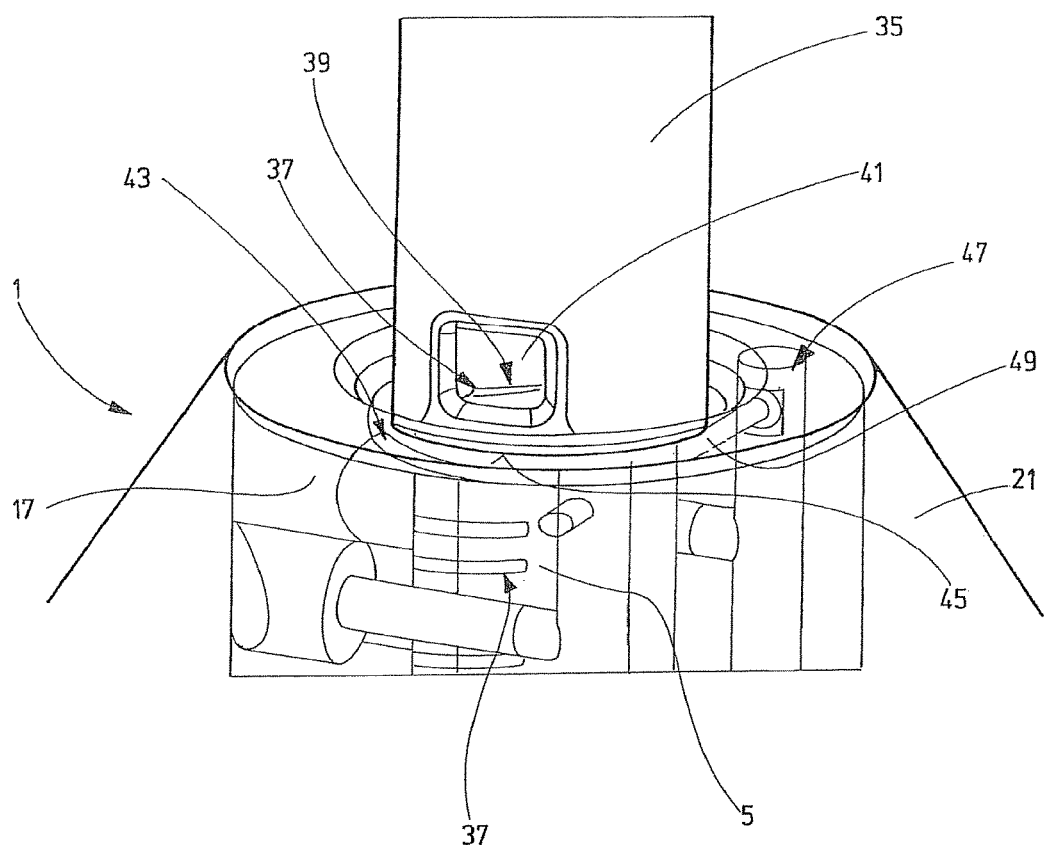
Figure 5:
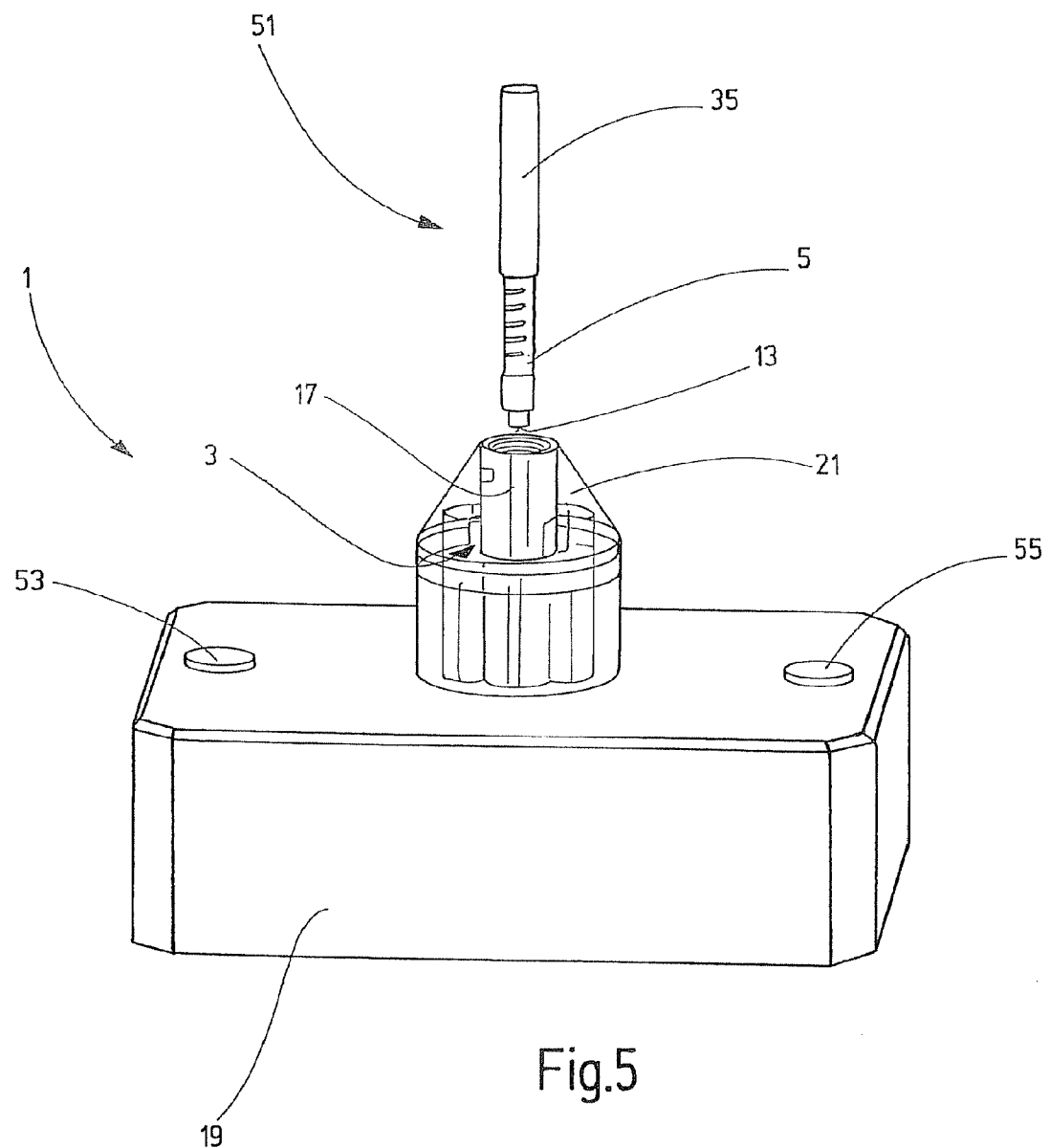

In the following, the invention will be explained in greater detail, using the drawing. This shows:

FIG. 1 a front view of a device for assembly of a pharmaceutical application aid, with a first housing sleeve;

FIG. 2 a front view of a device according to FIG. 1, with a first housing sleeve and a carpule;

FIG. 3 a perspective representation of a device according to the present teachings, with a first housing sleeve and a second housing sleeve;

FIG. 4 a detailed representation of the first housing sleeve and of the second housing sleeve in the assembled state; and FIG. 5 a front view of a device according to FIG. 1, with a finished, assembled application aid.

FIG. 1 shows a device 1 for assembly of a pharmaceutical application aid. The pharmaceutical application aid, in the example shown in FIG. 1, is a so-called auto-injector or pen. The device 1 comprises a holding device 3 that serves to fix a first housing sleeve 5 in place in a specific axial and/or radial position.

The holding device 3 can be implemented in different ways. For example, pneumatic, hydraulic or magnetic, but also manual activation of the holding device 3 is possible. In the exemplary embodiment shown here, the holding device 3 is implemented by means of a pneumatic cylinder 7 that activates two grippers 9 and 9', which bring about fixation of the first housing sleeve 5 both in the radial and in the axial direction. The point of engagement of the grippers 9 and 9' on the first housing sleeve 5 can fundamentally be chosen as desired.

The grippers 9 and 9' are moved toward one another during activation of the at least one pneumatic cylinder 7, so that the first housing sleeve 5 is firmly enclosed by the grippers 9 and 9'. In this connection, fixation of the first housing sleeve 5 must take place in such a manner that axial and radial displacement of the first housing sleeve 5 is prevented. Deactivation of the holding device 3 leads to the grippers 9 and 9' moving apart, so that the first housing sleeve 5 can be removed from the region of the holding device 3.

The device 1 has at least one first sensor 11 that detects a specific position of the first housing sleeve 5 in the region of the holding device 3. The first sensor 11 is preferably configured as a laser sensor that generates a signal if its laser beam is interrupted. Furthermore, it can advantageously be used to trigger activation of the holding device 3. As soon as the first housing sleeve 5 has been displaced so far into the device 1 that the lower end 13 of the first housing sleeve 5 interrupts the laser beam of the sensor 11, the holding device 3 is activated, so that the first housing sleeve 5 is fixed in place. In the example shown in FIG. 1, a laser beam runs perpendicular to the image plane in the region of the point indicated with L.

At the same time, or also alternatively to the first sensor 11, a stop element 15 can be provided, which is only indicated in FIG. 1. The stop element 15 serves to limit the displacement path of the first housing sleeve 5 in the device 1 and furthermore to create a defined relative position between the first housing sleeve 5 and the holding device 3. The laser beam at the point L is preferably disposed in the region of the stop element 15, so that therefore, a first housing sleeve 5, which is introduced into the device 1 by hand and reaches the stop element 15, is detected by the first sensor 11, and generates a corresponding signal for activation of the holding device 3.

Fundamentally, activation of the holding device 3 by the operating personnel is also possible, which personnel displaces the first housing sleeve 5 so far into the device 1 until it rests against the stop element 15, and therefore further displacement is no longer possible. In this connection, however, tilting of the first housing sleeve 5 can come about, for example in an accommodation unit 17 that particularly serves to guide the first housing sleeve 5, so that the housing sleeve 5 is not grasped by the holding device 3, or at least not grasped in the correct position. The first sensor 11 therefore serves to ensure that the first housing sleeve 5 is disposed in the correct position relative to the holding device 3. On the other hand, it is also possible to exclusively provide a first sensor 11 for positioning of the first housing sleeve 5, as was already explained above. The deciding factor is that the first housing sleeve 5 is fixed in place in a defined position by the holding device 3.

The accommodation unit 17 particularly serves to accommodate the first housing sleeve 5 and to guide it. It encloses the first housing sleeve 5 at least in certain regions, as shown in FIG. 1. The holding device 3 can furthermore engage into the accommodation unit 17, for example through openings that are provided in the accommodation unit 17 and through which the grippers 9, 9' of the holding device 3 can engage on the first housing sleeve 5.

The device 1 preferably also has a base body 19 in which electrical and/or pneumatic or other means, for example, are disposed. The device 1 shown in FIG. 1 furthermore has a mantling 21 that is supposed to serve, for one thing, to protect sensor elements, such as the first sensor 11 and the holding device 3. The mantling 21 furthermore improves the optical appearance of the device 1 and supports the holding device 3 as well as the accommodation unit 17.

FIG. 2 shows a front view of the device 1 according to FIG. 1. The same parts are provided with the same reference symbols, so that in this regard, reference is made to the description of FIG. 1.

In FIG. 2, again, the first housing sleeve 5 is disposed in the device 1. As indicated in the figure, a carpule 23 is inserted, by hand, into the first housing sleeve 5 held by the holding device 3. This is a dual-chamber carpule, for example; however, the use of a conventional carpule is also possible. The dual-chamber carpule comprises a first stopper 25 and a second stopper 27. By means of the second stopper 27, two chambers 29 and 31 are separated from one another, with a lyophilisate being situated in the chamber 31, and a fluid, preferably water, being situated in the chamber 29.

In the event of a displacement of the first stopper 25, a displacement of the stopper 27 also takes place, until the stopper has reached the region of a bypass 33. By way of the bypass 33, the fluid now gets out of the chamber 29 into the chamber 31, and mixes with the lyophilisate there. A displacement of the stopper 25 therefore leads to activation of the injection solution of the carpule 23. Activation of the carpule 23 is only supposed to take place when an injection is being performed by a patient.

FIG. 3 shows a perspective representation of a device 1 according to FIGS. 1 and 2. The same parts are provided with the same reference symbols, so that in this regard, reference is made to the description of the preceding figures.

In the device 1 shown in FIG. 3, the carpule 23 shown in FIG. 2 is situated in the first housing sleeve 5 and is therefore no longer visible. A second housing sleeve 35 is also shown in FIG. 3, which must be joined together with the first housing sleeve 5 in order to complete the assembly of the application aid. Purely as an example, the first housing sleeve 5 and the second housing sleeve 35 are joined together, here, by means of a screw connection. For this purpose, the first housing sleeve 5 comprises an outside thread 37, and the second housing sleeve 35 comprises a corresponding inside thread, which cannot be recognized here. However, joining the two housing sleeves 5 and 35 together can also take place by way of a plug-in connection or the like.

In the second housing sleeve 35, a piston rod, which cannot be recognized, is disposed, which serves to displace the stopper 25 shown in FIG. 2, to activate the carpule 23, if necessary. In the semi-automatic assembly of application aids, in which the second housing sleeve 35 is therefore set onto or screwed onto the first housing sleeve 5 not by machine, but rather manually, it is of particular importance that the second housing sleeve 35 is not screwed/set too far onto the first housing sleeve 5, since otherwise, the piston rod disposed in the second housing sleeve 35 comes into contact with the first stopper 25 shown in FIG. 2, and displaces it in the carpule 23, causing the lyophilisate to mix with the fluid. In the case of a conventional carpule, not shown, it could furthermore come about that injection fluid exits from the carpule during assembly. In order to prevent this, the second housing sleeve 35 should be screwed onto the first housing sleeve 5 only with a specific number of rotations, for example with one rotation. In manual assembly, however, over-tightening can very easily occur here.

FIG. 4 shows an enlarged representation of the upper end section of the second housing sleeve 35, which was joined together with the first housing sleeve 5. The same parts are provided with the same reference symbols, so that in this regard, reference is made to the description of the preceding figures.

When the second housing sleeve 35 is screwed onto the first housing sleeve 5, after one revolution, a thread section 39 of the outer thread 37 of the first housing sleeve 5 engages into an opening 41 of the second housing sleeve 35. In order to prevent further rotation of the second housing sleeve 35 by the operating personnel, a stop 43 is provided, against which the lower end 45 of the second housing sleeve 35 makes contact, as soon as the second housing sleeve 35 was attached to the first housing sleeve 5 with one revolution. The stop 43 can also be provided only after two or more rotations of the second housing sleeve 35 on the first housing sleeve 5. The deciding factor is that further rotation of the second housing sleeve 35 is effectively prevented by the stop 43.

The distance between the stop element 15, not shown in FIG. 4, and the stop 43 is dimensioned in such a manner that when the lower end 45 of the second housing sleeve 35 lies against the stop 43, no displacement of the first stopper 25 of the carpule 23 takes place by means of the piston rod, not shown, disposed in the second housing sleeve 35.

Joining together the second housing sleeve 35 with the first housing sleeve 5 is not restricted to a screw connection; instead, this can also be a plug-in connection with engagement elements. Other types of connections between the two housing sleeves are also possible. The deciding factor is merely that a relative displacement between the first housing sleeve 5 and the second housing sleeve 35 is limited by the stop 43 and the holding device 3.

In the example shown in FIG. 4, the stop 43 is configured in one piece with the accommodation unit 17. There, the stop 43 is introduced into the accommodation unit 17 in the form of a shoulder. However, other implementations of the stop 43 are also possible, for example by means of a free-standing element or by means of a one-piece configuration with the holding device 3.

According to FIG. 4, the device 1 also has a second sensor 47, which is preferably configured as a laser sensor and disposed in the region of the stop 43. In particular, it is provided that the second sensor 47 generates a signal as soon as its laser beam 49 is interrupted by the second housing sleeve 35, when the latter is joined together with the first housing sleeve 5. The second sensor 47 therefore detects when the second housing sleeve 45 comes to lie against the stop 43. The second sensor 47 preferably interacts with the holding device 3, not shown in FIG. 4, and deactivates it when the second housing sleeve 35 has reached the stop 43.

FIG. 5 shows the device 1 according to FIGS. 1 to 3. The same parts are provided with the same reference symbols, so that in this regard, as well, reference is made to the description of the preceding figures.

FIG. 5 makes it clear that after the second housing sleeve 35 has been joined together with the first housing sleeve 5, the application aid 51 can be removed from the device 1. If an injection by means of the pen is needed, the user can screw the second housing sleeve 35 further onto the first housing sleeve 5, in order to trigger activation of the carpule contents.

It also becomes clear that the holding device 3, the accommodation unit 17, and the mantling 29 are disposed on the base body 19. Furthermore, display elements 53 and 55 are provided on the base body 19, which elements preferably interact with the first sensor 11, which cannot be recognized, and the second sensor 47. For example, it can be provided that as soon as the first sensor 11 has detected the correct position of the first housing sleeve 5 in the device 1, a corresponding signal is transmitted to one of the display elements 53 or 55, in order to indicate to the operating personnel that the holding device 3 is fixing the first housing sleeve 5 in place, and that it is now possible to join it together with the second housing sleeve 35.

It is also possible that the second sensor 47 transmits a signal to one of the display elements 53 or 55, in order to indicate to the operating personnel that the second housing sleeve 35 was applied to the first housing sleeve 5, all the way to the stop 43.

It is also possible to implement acoustical signals that indicate the corresponding states of the device 1 to the operating personnel. After the two housing sleeves 5 and 35 have been joined together, it is also possible that a corresponding signal is transmitted from the second sensor 47 to the holding device 3, in order to deactivate it. For safety reasons, however, manual detection of the holding device 3 by the operating personnel is also possible.

From the explanations of the figures, it becomes clear that here, a special application aid assembly device was created, which serves to produce application aids with very great production security. In particular, containers that serve to accommodate a pharmaceutical product can be introduced into the application aid with great security. For this purpose, they are introduced into two housing sleeves that jointly enclose a cavity for accommodating the container, and are configured in such a manner that the pharmaceutical product can be dispensed from the container. In this connection, it is also possible to first activate a container that is configured as a two-chamber system, and to mix a lyophilisate with a solvent, in order to produce a pharmaceutical product. This can then be supplied to a patient during one or more application steps.

The application aid assembly device guarantees that the container accommodated by the housing sleeves is not impaired during assembly of the application aid, either in that the pharmaceutical product is already dispensed, at least in part, or that a two-chamber system is already unintentionally activated during assembly of the pharmaceutical application aid.

In the following, the function of the device described here, and the method for assembly of a pharmaceutical application aid, preferably a pen or an auto-injector, will be discussed in greater detail.

The advantageous method first of all requires making available a first housing sleeve 5. In the exemplary embodiment of the device 1 shown in FIG. 1, the first housing sleeve 5 is made available by the accommodation unit 17 and the stop element 15 that is indicated, so that the first housing sleeve 5 is therefore guided in the accommodation unit 17 until it reaches the stop element 15.

The method furthermore comprises the subsequent activation of the holding device 3 for fixation of the first housing sleeve 5 in a specific position. In order to reach the specific position, the housing sleeve 5 is preferably displaced up to the stop element 15. In addition, or also as an alternative to the stop element 15, it can be provided that the first sensor 11 detects when the first housing sleeve 5 has reached the specific position. Activation of the holding device 3 can take place either manually, by the operator, or automatically, by way of a corresponding signal from the sensor 11.

In order to complete the application aid 51, it is furthermore necessary to introduce a pharmaceutical container, preferably a carpule 23, into the first housing sleeve 5. The pharmaceutical container can be a two-chamber system, also referred to as a dual-chamber carpule, or a conventional carpule.

After fixation of the first housing sleeve 5 by means of the holding device 3, it is joined together with the second housing sleeve 35. This can be done, for example, by way of a screw connection or a plug-in connection. After the two housing sleeves 5 and 35 have been joined together, displacement of the second housing sleeve 35 relative to the first housing sleeve 5 takes place, until the second housing sleeve 35 reaches the stop 34. As a result of the fixation of the first housing sleeve 5 by means of the holding device 3, and, on the other hand, the contact of the second housing sleeve 35 on the stop 43, further displacement of the two housing sleeves 5 and 35 on one another is excluded.

In addition, it can be provided that a second sensor 47 detects when the second threaded sleeve 35 has reached the stop 43. Both the first sensor 11 and the second sensor 47 can interact with the holding device 3, with the first sensor 11 activating the holding device 3 and the second sensor 47 deactivating the holding device 3. The two sensors 11 and 47 can furthermore interact with display elements 53 and 55. The sensors 11, 47 are preferably configured as laser sensors, but any other type of sensor is also possible, if it is suitable for detecting the positions of the housing sleeves 5 and 35. In particular, it can be provided that multiple first and second sensors are provided. The holding device 3 preferably comprises pneumatic elements, but hydraulic or magnetic elements can also be provided. The holding device 3 can thus be implemented in the most different ways.

Furthermore, a third sensor, not shown, can also be provided, which preferably detects, through the opening of the first housing sleeve 5 in the region of the lower end 13, whether the carpule 23 is situated in the first housing sleeve 5, and, in the event of the presence of the carpule 23, generates a corresponding signal. The third sensor, too, can interact with a display element 53, 55, for example a green LED or the like, so that it is indicated to the operating personnel if the carpule 23 is disposed at the correct position in the first housing sleeve 5, and the second housing sleeve 35 can be joined together with the first housing sleeve 5. If the carpule 23 has not been correctly placed into the first housing sleeve 5, a corresponding signal can also be generated and transmitted to a corresponding display element 53, 55, for example a red LED. Furthermore, just like the first sensor 11 and the second sensor 47, it can be configured as a laser sensor, but any other suitable type of sensor can also be used. It can also be provided to provide multiple sensors for the monitoring described here, in place of the third sensor.

In total, it has been shown that in the advantageous device 1 for assembly of a pharmaceutical application aid 51 proposed here, multiple sensors, preferably three sensors, detect correct positioning of both the first and second housing sleeve and of the carpule 23. In case of an error, in other words if one of the aforementioned elements was not positioned correctly, the corresponding sensor transmits a(n) (error) signal to a related display element 53, 55, which indicates the incorrect positioning to the operator, by means of an optical or also an acoustical signal.

Incorrect positioning of the first housing sleeve 5 in the holding device 3 can be present, for example, if it does not reach its specific position, which was explained in greater detail in the description of FIG. 1, for example due to tilting in the accommodation unit 17. Incorrect positioning of the second housing sleeve 35, on the other hand, can be present if it does not reach its end position, namely the stop 43. It is also possible that the carpule 23 tilts when it is introduced into the first housing sleeve 5, and therefore cannot assume its correct position in the first housing sleeve 5.

If at least one of the error cases described above is present, it is preferably provided that an appropriately trained operator can remove the defective pen from the device 1, exclusively by means of a key switch, not shown. Operation of the switch can therefore only take place by means of a key to which only specific persons have access. The switch can then deactivate a locking mechanism, not described in greater detail here, which is activated as soon as one of the sensors has generated an error signal. Because only specific persons can remove a defective pen from the device 1 by means of the key switch, defective pens are prevented from being accidentally mixed together with defect-free pens.

The deciding factor is that fixation of the first housing sleeve 5 in a specific position takes place, and that the subsequent displacement of the second housing sleeve 35 relative to the first housing sleeve 5 is limited by a stop.

From the explanations both regarding the device for assembly of a pharmaceutical application aid and regarding the method for assembly of such an application aid, it becomes clear that the problems that exist in connection with assembly of an application aid by means of conventional devices can be eliminated in that a device of the type described here is used for the purpose of assembling an application aid. In particular, it is ensured that a pharmaceutical container can be enclosed in two housing sleeves, without damage or impairment of the container coming about. It is therefore ensured that pharmaceuticals do not exit from the container already during assembly of the pharmaceutical application aid, thereby making the application aid unusable. It is also avoided that a container configured as a two-chamber system is already unintentionally activated during assembly of the pharmaceutical application aid, and thus is fundamentally unusable.

Furthermore, it becomes clear that when using a device as described here, the method for assembly of a pharmaceutical application aid can be carried out without problems, and that a high level of production security can be guaranteed in this connection.

The invention claimed is:

1. An assembly device for assembly of a pharmaceutical application pen having a first housing sleeve for receiving a carpule and a second housing sleeve, the second housing sleeve displaceable a first axial distance relative to the first housing sleeve for assembly of the pharmaceutical application pen and displaceable a second distance for dispensing a treatment from the pharmaceutical application pen, the device comprising: an accommodation unit for accommodating and guiding the first housing sleeve; a holding device for fixating the first housing sleeve within the device; a stop element for limiting insertion of the first housing sleeve into the device in an axial direction; a stop for abutting a surface of the second housing sleeve and limiting displacement of the second housing sleeve relative to the first housing sleeve in the axial direction; and a first sensor for sensing a specific position of the first housing sleeve within the device, the first sensor operative to automatically activate the holding device to fixate the first housing sleeve within the device upon sensing of the first housing sleeve in the specific position.

2. The assembly device for assembly of a pharmaceutical application pen of claim 1, wherein the holding device fixates the first housing sleeve within the device in both a radial direction and an axial direction.

3. The assembly device for assembly of a pharmaceutical application pen of claim 1, wherein the stop is defined by the accommodation unit.

4. The assembly device for assembly of a pharmaceutical application pen of claim 3, wherein the stop is a shoulder of the accommodation unit.

5. The assembly device for assembly of a pharmaceutical application pen of claim 1, wherein the stop element is axially spaced from the stop.

6. The assembly device for assembly of a pharmaceutical application pen of claim 1, wherein the accommodation unit is generally cylindrical and defines an opening for receiving the first housing sleeve.

7. The assembly device for assembly of a pharmaceutical application pen of claim 1, wherein the holding device extends through openings in the accommodation unit for engaging the first housing sleeve.

8. The assembly device for assembly of a pharmaceutical application pen of claim 1, further comprising a mantling circumferentially surrounding the holding device and the accommodation unit.

9. The assembly device for assembly of a pharmaceutical application pen of claim 1, wherein the first sensor is a laser sensor.

10. The assembly device for assembly of a pharmaceutical application pen of claim 1, further comprising a second sensor for detecting when the second housing sleeve abuts the stop.

11. The assembly device for assembly of a pharmaceutical application pen of claim 10, wherein the second sensor is operative to deactivate the holding device when the second housing sleeve reaches the stop.

12. The assembly device for assembly of a pharmaceutical application pen of claim 10, wherein the second sensor is a laser sensor.

13. The assembly device for assembly of a pharmaceutical application pen of claim 1, in combination with the pharmaceutical application pen.

14. The assembly device for assembly of a pharmaceutical application pen of claim 13, wherein in the combination, the carpule is a dual-chamber carpule including a first stopper and a second stopper, the second stopper separating first and second chambers from one another, a lyophilisate situated in the first chamber and a liquid situated in the second chamber.

15. The assembly device for assembly of a pharmaceutical application pen of claim 14, wherein in the combination, the first housing sleeve and the second housing sleeve are rotatably joined to one another with a thread connection.

16. The assembly device of for assembly of a pharmaceutical application pen claim 1, wherein the assembly device is separate and distinct from the pharmaceutical application pen.

17. The assembly device for assembly of a pharmaceutical application pen of claim 1, wherein the accommodation unit defines an axially extending opening for receiving the first housing sleeve.

18. The assembly device for assembly of a pharmaceutical application pen of claim 17, wherein the stop element is disposed in the axially extending opening for stopping insertion of the first housing sleeve into the axially extending opening.

19. The assembly device for assembly of a pharmaceutical application pen of claim 1, wherein the accommodation unit encloses at least certain regions of the first housing sleeve.

20. The assembly device for assembly of a pharmaceutical application pen of claim 1, wherein the accommodation unit defines an axially extending opening for receiving the first housing sleeve.

21. An assembly device for assembly of a pharmaceutical application pen having a first housing sleeve for receiving a carpule and a second housing sleeve, the second housing sleeve displaceable a first axial distance relative to the first housing sleeve for assembly of the pharmaceutical application pen and displaceable a second distance for dispensing a treatment from the pharmaceutical application pen, the device comprising: an accommodation unit for accommodating and guiding the first housing sleeve; a holding device for fixating the first housing sleeve within the device; a stop element for limiting insertion of the first housing sleeve into the device in an axial direction; and a stop for abutting a surface of the second housing sleeve and limiting displacement of the second housing sleeve relative to the first housing sleeve in the axial direction; and at least one sensor selected from a first sensor for sensing a specific position of the first housing sleeve within the device and a second sensor for detecting when the second housing sleeve abuts the stop, wherein the at least one sensor is a laser sensor.

* * * * *